United States Patent [19]

Tsutsumi

[11] Patent Number: 5,629,211
[45] Date of Patent: May 13, 1997

[54] VETERINARY DIAGNOSTIC TEST

[75] Inventor: Kazuhiro Tsutsumi, Sakata-gun, Japan

[73] Assignee: Hiroshi Maeda, Hyogo, Japan

[21] Appl. No.: 642,409

[22] Filed: May 3, 1996

Related U.S. Application Data

[63] Continuation of Ser. No. 284,261, Aug. 2, 1994, abandoned.

[30] Foreign Application Priority Data

Aug. 2, 1993 [JP] Japan ................. 5-191201

[51] Int. Cl.$^6$ ............................................... G01N 33/20
[52] U.S. Cl. ................. 436/74; 436/73; 436/79
[58] Field of Search ................. 436/74, 79, 8, 436/16, 19, 73

[56] References Cited

U.S. PATENT DOCUMENTS

| | | | |
|---|---|---|---|
| 2,824,842 | 2/1958 | Sulkovitch | 436/74 |
| 3,121,613 | 2/1964 | Bittner | 436/79 |
| 3,754,864 | 8/1973 | Gindler | 436/74 |
| 3,912,454 | 10/1975 | Snyder | 436/77 |
| 4,205,953 | 6/1980 | Miller | 436/79 |
| 4,383,043 | 5/1983 | Denney et al. | 436/74 |
| 4,448,889 | 5/1984 | Neri et al. | 436/74 |
| 4,503,156 | 3/1985 | Yamazato et al. | 436/79 |
| 5,057,435 | 10/1991 | Denney | 436/79 |
| 5,215,922 | 6/1993 | Artiss et al. | 436/16 |
| 5,262,330 | 11/1993 | Chapoteau et al. | 436/79 |
| 5,376,552 | 12/1994 | Tokuda | 436/73 |
| 5,397,710 | 3/1995 | Steinman | 436/79 |
| 5,409,814 | 4/1995 | Berry et al. | 435/22 |

OTHER PUBLICATIONS

Lamkin et al., Spectrophotometric Determination of Calcium and Magnesium in Blood Serum with Arsenazo and EGTA Anal. Chem. 37, 8, 1965 pp. 1029–1031.
Marczenko, Separation and Spectrophotometric Determenation of Elements. Ellis Horwood Limited 1986 pp. 356–359.
Mann et al. Spectrophotometric Determination of Magnesium with Sodium, 1–Azo–2–hydroxy–3–(2,4–dimethylcarboxanilido)–naphtalete–1–(2–hydroxy-benzene–5–sulfonate) Anal. Chem. 28, 2, 1956 pp. 202–205.
Aldrich Chemical Co, Catalog, 1992, pp. 1267, 1288, 556, 586, 589, 1157.

*Primary Examiner*—Jill Warden
*Assistant Examiner*—Alexander Markoff
*Attorney, Agent, or Firm*—Schweitzer Cornman & Gross

[57] ABSTRACT

A composite reagent, for a veterinary diagnostic test, which contains a color reagent substance to produce a color by reacting with either one or both of magnesium (Mg) ions and calcium (Ca) ions, a polyoxyethylene alkylphenyl ether, and a masking agent for interfering metal ions in a urine of an animal other than the Mg ions and the Ca ions.

3 Claims, No Drawings

VETERINARY DIAGNOSTIC TEST

This is a continuation of patent application Ser. No. 08/284,261, filed on Aug. 2, 1994, now abandoned.

FIELD OF THE INVENTION

The present invention relates to a composite reagent for a veterinary diagnostics, which helps in diagnosing or confirming the presence of a urinary calculus and diseases of the urinary tract in animals, such as dogs and cats.

BACKGROUND OF THE INVENTION

Diseases of the animal urinary tract have prevailed in recent years among many pets such as dogs and cats, and the incidence of such diseases is now increasing. Major causes of such diseases have been believed to be physical discomfort due to lack of exercise because many of pets are kept indoors by a recent change of urbanized human living environment, and in that the ready-made foods sold for pets are limited in kinds and are biased in nutrition. However, these are mere suppositions. The true causes of animal urinary tract diseases have not been determined as yet.

In veterinary medicine, it is required to counteract the expansion of the diseases of the animal urinary tract with a simple diagnostic method of such diseases by external observation. However, at this time there is no externally observable simple diagnostic test available, because there has not been found any practical reagent and means which are useful to detect diseases of the animal urinary tract. There was some speculation that an alkaline urine is indicative of such a disease, however, it has been proven that the relationship does not always exist between the alkaline urine and such diseases because phosphorus ions or the like from the pet food strongly affect the urine.

Metal ions in the urine can also be determined by enzymolysis. However, this method is not practical because it requires a relatively expensive reagent prepared by a complicated process. It has inferior shelf life (about one month even when preserved in a refrigerator), and it has a low reactivity and reliability. The reagent is inconvenient to handle and a test solution of the reagent is clear so that a quantitative determination can be made only by absorptiometry and thus a simple diagnosis by external observation is impossible.

SUMMARY OF THE INVENTION

It is, therefore, an objective of the present invention to provide a composite reagent which can provide an observable diagnostic test for diseases of the animal urinary tract, i.e. to provide a composite reagent which can detect the relevant factors of the diseases of the animal urinary tract from the animal urine quantitatively by a process of chemical color change to enable diagnosis the presence and degree of such diseases correctly by external observation of coloration of a test solution.

It is another objective of the present invention to provide a composite reagent, for an observable veterinary diagnostic test, which can be produced readily at low cost with superior stability and preservation of reactivity with good shelf life.

With the above and other objectives in view, the present invention provides a composite reagent, for a veterinary diagnostic test, which contains a color reagent to produce a color by reaction with either one or both of magnesium and calcium ions, a polyoxyethylene alkylphenyl ether, and a masking agent for interfering metal ions in the urine of an animal, other than Mg, and Ca ions.

The veterinary diagnostic test is conducted with the reagent of the present invention by treating a small amount of the urine of an animal with a solution of the composite reagent of the invention. If there are Mg ions or/and Ca ions in the animal urine, the composite reagent reacts with them to reveal a color of a color saturation that is proportional to the concentration of these ions. It is well known that magnesium and calcium ions are in the urine of animals suffering from urine discharge disorders, such as dysuria and urinary retention due to the urinary calculus and diseases of the urinary tract such as hematuria and systitis. Therefore, the coloration of the test solution enables early and easy diagnosis of such disorders and their degree from the color saturation. This enables remedial treatment for example, to promote the discharge of the urine by administering diuretics in the case of a slight disorder, or to take a surgical measure against more serious conditions. If need be, the Mg and Ca ions can be quantitatively determined more accurately by applying an absorptiometer to the coloration of the test solution, so that a more correct diagnosis can be made.

DETAILED DESCRIPTION OF THE INVENTION

The composite veterinary diagnostic reagent of the present invention is formed by mixing a color reagent substance to react with specified metal ions, a polyoxyethylene alkylphenyl ether, and a masking agent for interfering metal ions other than the specified metal ions to be determined in the urine of an animal.

The color reagent for revealing a color by reaction with Mg ions or/and Ca ions is suitably xylylazo violet-1, also known as xylidyl blue-1. It is stable and reactive and thus an ideal reagent with good shelf life and reliable operation. A xylylazo violet-1 is the sodium salt of 1-azo-2-hydroxy-3-(2,4-dimethylcarboxy anilide)-naphthalene-1'-(2 hydroxybenzene-5-sulfonic acid), and produces a color by chelation in which —OH group is replaced by the bivalent magnesium or calcium ions. The resulting color is reddish violet of pH 11 or higher. Xylylazo violet-1 has the formula:

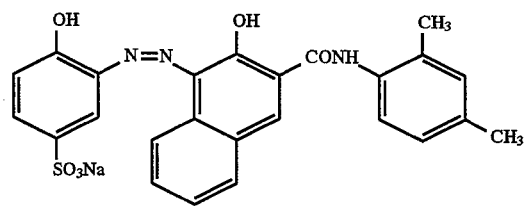

The polyoxyethylene alkylphenyl ether, component of the aforementioned composite reagent, is a nonionic surfactant with ampholytic property, and is used in the reagent to solubilize the fat and protein molecules in the animal urine to enhance the stable coloration of the color reagent. When xylylazo violet-1 is used as the color reagent, the polyoxyethylene alkylphenyl ether also acts as a promoter for solubility of the composite reagent in water. The polyoxyethylene alkylphenyl ether suitably has an isooctyl group as its alkyl groups, and it is suitably polyoxyethylenated with 9 or 10 groups of oxyethylene in its formula $(CH_2CH_2O)_nH$.

The masking agent in the reagent of the present invention, suitably a triethanolamine (TEA), can be used to mask ferric and ferrous ions; ethylene glycolbis (2-aminoethyl ether) N,N'-tetraacetic acid (EGTA) for masking manganese and nickel ions; and a tetraethylene pentaamine (TEPA) for masking cobalt, nickel, copper, and zinc ions. For the pets such as dogs and cats, TEA and EGTA are used together. To detect only the Mg ions suitably a separate masking agent is used for the Ca ions, for example a sulfate ion donor such as $Na_2SO_4$, together with any of the aforementioned masking compounds for the interfering metal ions.

When the masking agent is to contain TEA and EGTA, it eliminates interference of metal ions in the animal urine and enables correct diagnosis.

The composite reagent of the present invention can be produced in various forms, can be produced in various forms, such as an aqueous solution, a mixed powder, or granules, or a tablet shaped by a water-soluble binder such as dextrin. The finished product of the composite reagent is very stable in every form and is reactive in the test even when used after a long period of preservation at room temperature. When the composite reagent is a powder or other solid, it is made suitable for the test by dissolving it in water.

The composite reagent of the present invention is suitably prepared from its aforementioned three constituents by mixing with 1 part by weight of the color reagent, 50 to 200 (suitably 80 to 150) parts by weight of the polyoxyethylene alkylphenyl ether, and 70 to 300 (suitably 100 to 200) parts by weight of the masking agent. When TEA and EGTA are used together as the masking agent, a suitable weight ratio of TEA to EGTA is 1:1.5 to 1:4.

The veterinary diagnostic test is conducted simply by treating a certain quantity of the animal urine with the test solution of the composite reagent of the present invention in water. However, to prevent a change in coloration due to a change of pH it is desirable to add a buffer to the reagent solution such as water-soluble phosphate, e.g. sodium hydrogenphosphate and alkali compounds such as sodium hydroxide. When xylylazo violet-1 is used as a color reagent, the buffer should be prepared so that the test solution of the composite reagent can be kept at pH 11–12 in the coloration range of reddish violet.

EXAMPLE

|  | (parts by weight) |
|---|---|
| xylylazo violet-1 | 0.1 |
| polyoxyethylene alkylphenyl ether | 10.3 |
| (Triton X-100 manufactured by E. I. DuPont |  |
| TEA | 5.0 |
| EGTA | 1.6 |
| sodium hydrogenphosphate | 71.6 |
| sodium hydroxide | 5.0 |
| water | 897.4 |

The above test solution is a clear colorless liquid of pH 11.7. The test was conducted on 0.5 ml of each urine sample each mixed with 10 milliliter test solution. After five minutes, the coloration of color change of each treated solution was visually observed. The degree of the color saturation of each solution was determined by comparison with a chart representing grades of color saturation, whereby the higher the color saturation, the greater the test result which is a number that is related to the concentration of the tested metal. The result of such observation and determination is listed in the following Table together with the names of diseases or disorders diagnosed clinically by a veterinarian, the amount of magnesium in the respective urines measured by means of titan yellow, and the presence of the urinary calculus confirmed by dropping ammonia (the sign + means existence, the sign − means absence). The aforementioned urine samples each were obtained from the respective animals by compression of the urinary bladder, ureteral catheterization, or by spontaneous discharge of urine.

| Animals; Age | Diseases or Disorders | Colors and Grades of saturation | Amount of Mg (milligram/one day) | Urinary calculus |
|---|---|---|---|---|
| Cat A;7 | Urinary retention | reddish violet +1.5 | 1.1 | + |
| Cat B;5 | Urinary retention | reddish violet +1.5 | 4.2 | + |
| Cat C;3 | Urinary retention | reddish violet +2.5 | 1.9 | + |
| Cat D;8 | Urinary retention | reddish violet +1.8 | 0.5 | + |
| Cat E;5 | Urinary retention | reddish violet +0.6 | 0.6 | + |
| Cat F;3 | Urinary retention | reddish violet +1.8 | 7.0 | + |
| Cat G;3 | Urinary retention | reddish violet +4.0 | 19.0 | + |
| Cat H;5 | Urinary retention | reddish violet +2.0 | 3.3 | + |
| Cat I;2 | Normal health | No coloration (*1) | below 0.1 | − |
| Cat J;4 | Normal health | No coloration | below 0.1 | − |
| Cat K;2 | Normal health | No coloration | below 0.1 | − |
| Dog A;5 | Urinary retention | No coloration (*2) | 2.4 | + |
| Dog B;10 | Urinary retention | reddish violet +1.0 | 0.6 | + |

(*1) The urine was taken from the Cat I neutered two months before.
(*2) No coloration in five minutes, but the color of reddish violet of pH 11.5 was produced in ten minutes.

The Table shows that the urine of healthy animals remained unchanged in color by the test solution of the composite reagent of the present invention, whereas the urine of the animals which suffered from disorders or diseases of the urinary tract changed in color by the test solution, wherein the degree of color saturation of the urine was proportional to the magnesium concentration. The presence of a urinary calculus could also be diagnosed since it contains the magnesium salt struvite, and the calcium phosphate apatite, as well as calcium oxalate.

What is claimed is:

1. A diagnostic process to detect animal urinary tract disorders due to urinary calculus and diseases of the urinary tract characterized by presence of at least one of magnesium and calcium ions in urine the process comprising:

contacting a sample of animal urine with a solution of a composite reagent of (i) xylylazo violet-1 as a color reagent, (ii) a polyoxyethylene alkylphenylether as a surfactant, and (iii) a masking agent of a mixture of triethanolamine (TEA), and ethylene glycolbis (2-aminoethyl ether) N,N'-tetraacetyl acid (EGTA), in a 1:1.5 to 1:4 weight ratio;

observing a color change caused by the reaction of at least one of calcium and magnesium ions with said composite reagent; and relating said color change to animal urinary tract disorders.

2. The diagnostic process of claim 1, wherein said animal is a cat or a dog.

3. The diagnostic process of claim 1, wherein said solution has a pH of between 11 and 12.

* * * * *